United States Patent [19]
Bukatov et al.

[11] Patent Number: 4,957,503
[45] Date of Patent: Sep. 18, 1990

[54] HEART VALVE PROSTHESIS

[76] Inventors: Alexandr S. Bukatov, ploschad Pobedy, 1, korpus "A", kv. 122; Naum A. Iofis, Lomonosovsky prospekt, 23, kv. 416; Jury G. Egorov, Sevastopolsky prospekt, 83, korpus 1, kv. 28; Natalya B. Dobrova, ulitsa Matrosskaya tishina, 17, kv. 26; Anatoly S. Kostretsov, ulitsa Bakuninskaya, 10/12, kv. 7; Andrei V. Agafonov, ulitsa Smolnaya, 63, kv. 149, all of Moscow, U.S.S.R.

[21] Appl. No.: 335,790

[22] PCT Filed: Jun. 23, 1988

[86] PCT No.: PCT/SU88/00137
§ 371 Date: Feb. 24, 1989
§ 102(e) Date: Feb. 24, 1989

[87] PCT Pub. No.: WO88/10105
PCT Pub. Date: Dec. 29, 1988

[30] Foreign Application Priority Data
Jun. 25, 1987 [SU] U.S.S.R. .............. 4261093

[51] Int. Cl.$^5$ .............................................. A61F 2/24
[52] U.S. Cl. ........................................................ 623/2
[58] Field of Search .................. 623/2; 137/527, 527.8

[56] References Cited
U.S. PATENT DOCUMENTS
| | | | |
|---|---|---|---|
| 4,423,525 | 1/1984 | Vallana et al. | 623/2 |
| 4,713,071 | 12/1987 | Iofis et al. | 623/2 |
| 4,863,466 | 9/1989 | Schlegel | 623/6 |

Primary Examiner—Ronald Frinks
Attorney, Agent, or Firm—Burgess, Ryan & Wayne

[57] ABSTRACT

A heart valve prosthesis has a valve ring (1) having an opening (2) for the flow of blood. A valve poppet (3) is mounted in the opening (2) for closing and opening it. An annular curvilinear depression (9) is provided on an upper or distal side (6) of the poppet (3) for reducing the poppet mass. The poppet (4) is floatingly mounted between support structures (4, 5).

2 Claims, 1 Drawing Sheet

HEART VALVE PROSTHESIS

This is a continuing application, under the provisions of Title 35 U.S.C., Sections 365(a) and (b), and 120, of International application PCT/SU88/00137 with an international filing date of June 23, 1988 and a Russian application priority date of June 25, 1987.

FIELD OF THE ART

The invention relates to the medicine, and more specifically, it deals with cardiosurgery, and in particular, with a heart valve prosthesis designed for implantation to replace an affected natural heart valve.

STATE OF THE ART

In recent years so called poppet heart valve prostheses have come into a widespread use which comprise a valve ring or body having an opening for the flow of blood and a valve poppet mounted therein and designed for closing and opening the ring opening during operation of the valve. The poppet is floatingly mounted by means of upper and lower support structures which are essentially poppet motion limiters and hereinafter referred to as support structures. The poppet of such a valve has an upper or distal side and a lower or proximal side, the former being concave and having a depression for the upper support structure and the latter being shaped to fit configuration of the lower support structure, e.g. as shown in U.S. Pat. No. 4,057,857 to Fettel et al., or in U.S. Pat. No. 4,713,071 to Iotis et al.

Such valves have a certain advantage, e.g. they ensure a surface-to-surface contact of the poppet in the closed position with the support structures the latter reference, namely U.S. Pat. No. 4,713,071 teaching the provision of the surface-to-surface contact in both, open and closed positions of the valve poppet. At the same time, this type of the heart valve prosthesis features a rather massive poppet due to the fact that the distal side of the valve poppet is made convex whereby the volume, and, consequently the mass of the poppet increases. This circumstance, in turn, results in impared conditions for rehabilitation of a patient during postoperation period and hampers angular rotation of the poppet.

DISCLOSURE OF THE INVENTION

A problem now resides in the poppet of a heart valve prosthesis which is so constructed as to reduce its mass, thereby facilitating the angular rotation of the poppet, prolonging its service life and enhancing reliability of the valve in operation, whereby the rehabilitation conditions of a patient are also improved.

This technical problem is solved by that in a heart valve prosthesis comprising a valve ring having an opening for the flow of blood to pass and a valve poppet floatingly mounted in this opening and having a distal side and a proximal side engageable with support structures, according to the invention, the distal side has an annular concave portion which is located between the middle part of the distal side and the periphery of the poppet and which is smoothly conjugated with this periphery along the whole circumference of the poppet.

The provision of the concave portion makes it possible to achieve a substantial reduction of the poppet mass which is especially important upon a substantial deterioration of the cardiac muscle function. Although the angular motion in this case is ensured similarly to the prior art construction owing to a special design of the support structures, the reduction of the poppet mass enhances this angular motion because the lower the mass of the poppet, the better the conditions for its angular motion.

One embodiment of the invention envisages that the concave portion of the distal side and the proximal side have the same radius of curvature. This facilitates best hemodynamic conditions of the flow of blood in the opening of the valve ring.

BRIEF DESCRIPTION OF THE DRAWINGS

The invention will now be described with reference to specific embodiments which are given as non-limiting examples and which are illustrated in the accompanying drawings, in which.

PREFERRED EMBODIMENT OF THE INVENTION

Figure 1:
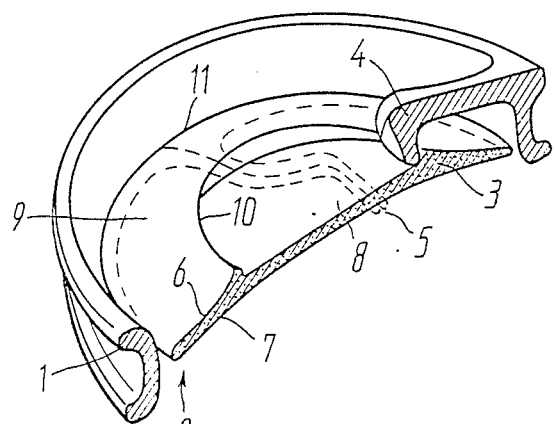
FIG. 1 is a perspective view, partially in section of a heart valve prosthesis illustrating one embodiment of the invention.

With reference, first, to FIG. 1, where the construction of a heart valve prosthesis according to the invention is best shown, the heart valve prosthesis comprises a valve ring or body 1 in the form of a cylinder with shoulders for attaching a collar (not shown in the drawings for the sake of clarity as it has no material bearing on this invention). Construction, configuration and material of such a collar are well known to those skilled in the art. The collar is designed for attaching the prosthesis to the surrounding tissues when the prosthesis is implanted. The valve ring 1 defines a valve opening 2 and a seat for a valve poppet 3. The poppet 3 is floatingly mounted as described in detail in U.S. Pat. No. 4,713,071, which is included in this specification by reference, and is held in this position by means of an upper support structure 4 and a lower support structure 5 of which only one half is shown in FIG. 1.

The poppet 3 has an upper or distal side 6 and a lower or proximal side 7. The proximal side is slightly concave and its radius of curvature is chosen to fit configuration of the lower support structure 5. A depression 8 for receiving the upper support structure 4 is provided in the central part of the distal side 6.

Figure 2:
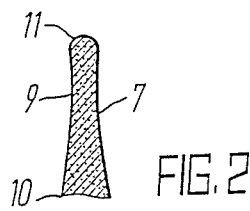
FIG. 2 a partial sectional view of a valve poppet of FIG. 1.

A portion 9 of the upper or distal side 6 of the poppet 3 is made concave between extremities 10 of the depression 8 and a periphery 11 of the poppet 3 along the whole circumference of the valve poppet. Radius of curvature of the concave portion in this specific embodiment is equal to radius of curvature of the proximal side 7 as can be seen in FIG. 2. It will be understood that radius of curvature of the concave portion may be other than radius of curvature of the proximal side 7. In general, curvature of the concave portion 9 is chosen in such a manner as to ensure smooth conjugation with the periphery 11 and not to impair geometrical parameters for the flow of blood when the valve poppet 3 is in the open position, i.e. so as not to cause an increase in hydraulic resistance.

The abovedescribed configuration of the distal side 6 which involves the provision of the concave portion 9 along the whole circumference of the poppet makes it possible to reduce the poppet mass without affecting its kinematic cooperation with the support structures and without deterioration of physiological properties of the heart valve prosthesis. It should be noted, that in case a poppet having a biconcave symmetrical configuration shown in FIG. 2 is used, hydraulic resistance is even lowered in comparison with prior art heart valve prostheses. It should also be noted that with this configuration of the poppet 3, it is preferred that the support structures be made in the manner provided for in U.S. Pat. No. 4,713,071 so as to ensure angular motion of the valve poppet 3. It should also be born in mind that the reduction of the valve poppet mass improves conditions for angular motions of the poppet in the flow of blood.

Operation of the abovedescribed heart valve prosthesis will not be discussed herein as this operation does not differ from that described in cited U.S. Pat. No. 4,713,071. It should be only noted that the use of this invention allows the poppet mass to be reduced by 15% in comparison with prior art constructions without any impairment of homodynamic parameters of the valve.

INDUSTRIAL APPLICABILITY

The valve prosthesis is widely used for the replacement of the aortic or mitral valve, especially in case of a substantial deterioration of the cardiac muscle function owing to a lower mass of the poppet. The poppet according to the invention is made of biologically inert materials such as titanium alloys or carbonbased materials.

We claim:
1. A heart valve prosthesis comprising:
    (a) a valve ring (1) having an opening (2) for the passage of blood, and suport structures (4,5); and
    (b) a valve poppet (3) floatingly mounted in the opening (2) and having a distal side (6) and a proximal side (7) engageable by the support structures (4,5) respectively, to thereby limit the motion of the poppet (3), said distal side (6) and proximal side (7) having a concave shape with a radius of curvature whose centers are on opposed sides of the valve, wherein a periphery of said distal side (6) and a periphery of said proximal side (7) form a smoothly surfaced edge along the entire circumference of the poppet (3) and said concave distal and proximal sides diverge inwardly away from said smoothly surfaced edge.
2. A heart valve prosthesis according to claim 1 in which the distal side (6) and the proximal side (7) have the same radius of curvature.

* * * * *